United States Patent [19]

Kim et al.

[11] Patent Number: 5,663,411
[45] Date of Patent: *Sep. 2, 1997

[54] (+)2-BENZOYL-3-[(PROP-2(S)-YL)AMINO] ACRYLATE DERIVATIVES AND A METHOD FOR THE PREPARATION OF THE SAME

[75] Inventors: Youseung Kim; Soon Bang Kang; Seonhee Park, all of Seoul, Rep. of Korea

[73] Assignee: Korea Institute of Science and Technology, Seoul, Rep. of Korea

[ * ] Notice: The term of this patent shall not extend beyond the expiration date of Pat. No. 5,491,251.

[21] Appl. No.: 321,359

[22] Filed: Oct. 11, 1994

[30] Foreign Application Priority Data

Mar. 22, 1994 [KR] Rep. of Korea .................. 5761/1994

[51] Int. Cl.⁶ .................. C07C 205/06; C07C 229/34
[52] U.S. Cl. .................. 560/22; 560/37
[58] Field of Search .................. 560/22, 37

[56] References Cited

U.S. PATENT DOCUMENTS 5,491,251  2/1996  Kim et al. .................. 560/23

OTHER PUBLICATIONS

Hayakawa, et al., "Synthesis an antibacterial Activities of Substituted 7-Oxo-2, 3-dihydro-7H-pyrido-[1,2,3,-de] [1,4] benzoxazine-6-carboxylic Acids", *Chem. Pharm. Bull.*, 32:4907-4913 (1984).

Schriewer et al., "Preparation of Chiral-bridged Quinolone Bactericides, including S-Ofloxacin", *Chem. Abstr.* 107:154342c (1987).

Mitscher et al., "Chiral DNA Gyrase Inhibitors. 2. Asymmetric Synthesis and Biological Activity of the Enantiomers of 9-Fluoro-3-methyl-10-(4-methyl-1-piperazinyl)-7-oxo-2,3-dihydro-7H-pyrido[1,2,3-de]-1, 4-benzoxazine-6-carboxylic Acid (Ofloxacin)", *J. Med. Chem.*, 30:2283 (1987).

Masuzawa et al., "Preparation of Pyridobenzoxazinone Analogs as Antibacterials", *Chem. Abstr.* 108:112468p (1988).

Egawa et al., "A Process for Preparation of 2,3-dihydro-7-oxo-7H-pyrido [1,2,3-de] benzoxanzine-6-carboxylates and intermediates thereof as Drugs and Drug Intermediates", *Chem. Abstr.* 108:167489b (1988).

*Primary Examiner*—Joseph Conrad
*Attorney, Agent, or Firm*—Townsend and Townsend and Crew LLP

[57] ABSTRACT

There are disclosed (+)2-benzoyl-3-[prop-2(S)-yl)amino] acrylate derivatives of following the formula and a method for the preparation of the same;

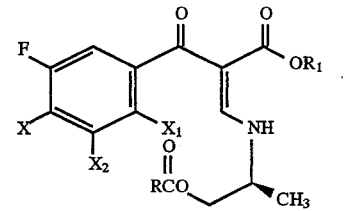

wherein X is a halogen; $X_1$ and $X_2$ are independently selected from a halogen and a nitro; and R and $R_1$ each is an alkyl group containing 1 to 4 carbon atoms.

4 Claims, No Drawings

(+)2-BENZOYL-3-[(PROP-2(S)-YL)AMINO] ACRYLATE DERIVATIVES AND A METHOD FOR THE PREPARATION OF THE SAME

BACKGROUND OF THE INVENTION

1. Field of the Invention

The present invention relates to (+)2-benzoyl-3-[(prop-2(S)-yl)amino]acrylate derivatives useful to synthesize antibacterially active (−) piperazine benzoxazine derivatives and a preparing method thereof.

2. Description of the Conventional Art

Intermediates for synthesis of (−)piperazine benzoxazine derivatives and preparing methods thereof are disclosed in German Patent No. 3,543,513; Chemical Abstract 107, 154342c (1987); L. A. Mitscher et al., J. Med. Chem., 30,2283 (1987)).

German Patent No. 3,543,513 (1987) and Chemical Abstract 107, 154342c (1987) relate compounds the type of

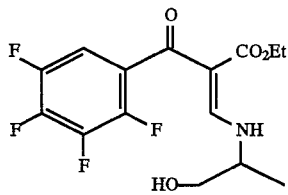

and a preparing method thereof. However, the preparation method comprising reacting ethyl ethoxymagnesium malonate with 2,3,4,5-tetrafluorobenzoyl chloride to give ethyl (2,3,4,5-tetrafluorobenzoyl)acetate, reacting the ethyl(2,3,4,5-tetrafluorobenzoyl)acetate with triethyl orthoformate and acetic anhydridechloride chloride, and substituting with 2-amino-1-propanol, is complicated and the product yield is relatively low.

DESCRIPTION OF THE INVENTION

The present invention relates to novel compounds useful to synthesize antibacterially active (−)piperazine benzoxazine derivatives. More particularly, the present invention is concerned with (+)2-benzoyl-3-[(prop-2(S)-yl)amino] acrylate derivatives having the following formula I or the salts thereof:

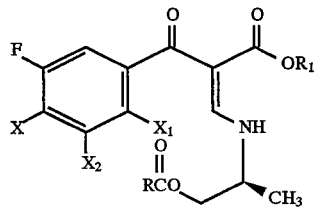

wherein X is a halogen; $X_1$ and $X_2$ are independently selected from halogen and nitro; and R and $R_1$ each is an alkyl group containing 1 to 4 carbon atoms.

This compound can be used as a starting material to synthesize the potent antibacterial compounds of (−)piperazine benzoxazine derivatives, especially (−)9-fluoro-7-oxo-2,3-dihydro-7H-pyrido[1,2,3-de]-1,4-benzoxazine-6-carboxylic acid derivatives. It proceeds to the antibacterial compound through (−) benzoxazine derivatives having the following formula II:

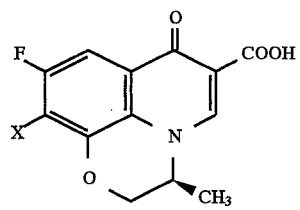

wherein X is halogen.

The antibacterial compounds produced from the compound of formula I and a preparing method thereof are described in detail in Korean Patent Application No. 5762/94 of the present inventors, filed on Mar. 22, 1994 incorporated herein by reference U.S. counterpart application No. 08/321,360.

The present invention is also concerned with a method for the preparation of (+)2-benzoyl-3-[(prop-2(S)-yl)amino] acrylate derivatives of the formula I.

The compounds of formula I can be obtained by reacting alkyl propiolate of the following formula III

wherein $R_1$ is an alkyl containing 1 to 4 carbon atoms, with (S)-(+)-2-amino-1-propanol of the following formula IV

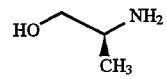

in an organic solvent, to give a (+) acrylate derivative of the following formula V

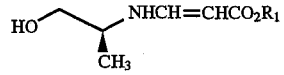

wherein $R_1$ is as defined hereinabove;

treating the (+) acrylate derivative of formula V with an acyl chloride derivative of the following formula VI

wherein R is an alkyl containing 1 to 4 carbon atoms, in the presence of a suitable base, to give a (+) alkylacrylate derivative of the following general formula VII

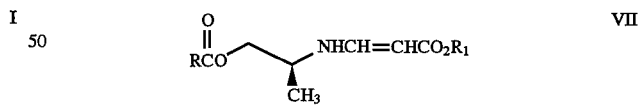

wherein $R_1$ and R are as defined hereinabove; and treating the (+) alkylacrylate derivative of formula VII with a benzoyl derivative of the following formula VIII

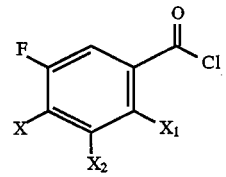

wherein X is a halogen; and $X_1$ and $X_2$ are independently selected from a halogen and nitro, in the presence of a suitable base.

In order to help understand the present invention, the preparation method of the present invention is summarized in the following scheme.

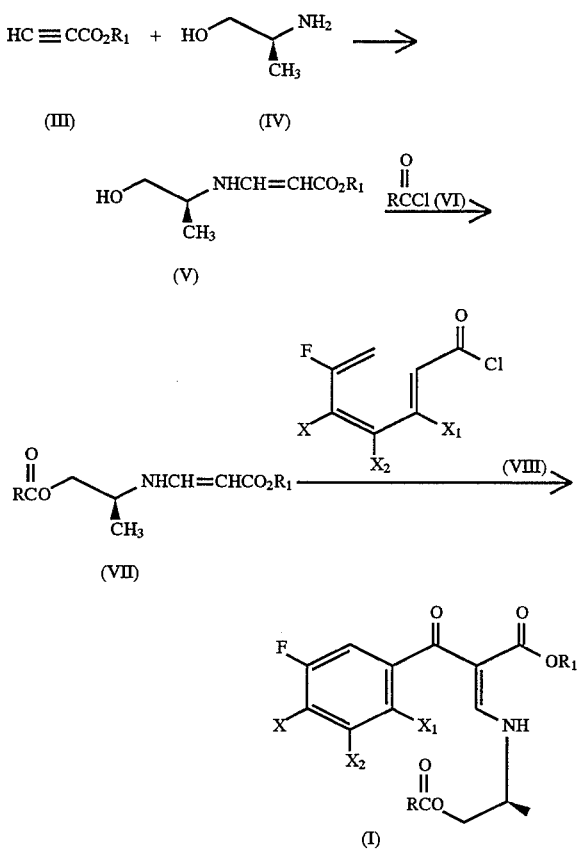

In accordance with a further aspect of the present invention, a compound of formula V, an intermediate useful to prepare the compound of formula I is provided.

In accordance with still a further aspect of the present invention, a compound of formula VII, another intermediate useful to prepare the compound of formula I is provided.

The organic solvent effective for the reaction of the compound of formula III with (S)-(+)-2-amino-1-propanol of formula IV includes acetonitrile, tetrahydrofuran, dimethylformamide, dioxane, dimethylacetamide, dimethylsulfoxide, chloroform, methylenechloride, ethylenechloride or diethylether. In the organic solvent, this reaction is carried out at a temperature of 0° to 25° C. for 1 to 10 hrs. In the reaction, the equivalent ratio of the compound of formula III to the compound of formula IV is preferably 1:1.

In an organic solvent, such as acetonitrile, tetrahydrofuran, methylene chloride, diethylether, ethylene chloride and chloroform, the compound of formula V is stirred along with the compound of formula VI at a temperature of 0° to 20° C. for 10 minutes to 2 hrs in the presence of the above-mentioned base, so as to give a (+)alkylacrylate derivative of formula VII, a novel compound. In this reaction, the equivalent ratio of the compound of formula V to the compound of formula VI to the base is preferably in the range of 1:1.1:1.1 to 1:1.1:1.5.

While being heated, the (+) alkylacrylate derivative of formula VII is stirred along with benzoyl chloride of formula VI in an organic solvent, such as acetonitrile, dimethylformamide, dimethylacetamide, tetrahydrofuran, dimethylsulfoxide, methylene chloride, chloroform and diethylether, at a temperature of 0° to 100° C. for 10 minutes to 2 hrs in the presence of base to yield (+)2-benzoyl-3-[(prop-2(S)-yl)amino]acrylate derivatives of formula I.

In this reaction, the equivalent ratio of the compound of formula VII to the compound of formula VIII to the base is preferably in the range of 1:1.1:1.2 to 1:1.2:1.5.

As a preferred base for the present invention, triethylamine, pyridine, potassium carbonate, sodium carbonate, calcium carbonate, 4-dimethylaminopyridine, 1,8-diazabicyclo[5.4.0] undec-7-en or 1,5-diazabicyclo[4.3.0] non-5-en can be used.

The products of those reactions including (+)2-benzoyl-3-[(prop-2(S)-yl)amino]acrylate derivatives of formula I, the (+)acrylate derivative of formula V and the (+)alkylacrylate derivative of formula VII can be separated and purified by conventional techniques, such as evaporation, filtration, extraction, chromatogaphy, distillation and the combinations thereof. For example, the mixture containing the product is initially dried under reduced pressure to condense it. The resultant residue is mixed with a mixture of water and an organic solvent, such as ethylene chloride, chloroform, diethylether or ethylacetate, and then the organic solvent is condensed to give a product. In case of the mixture of product and by-products, further purification may be performed by chromatography, re-distillation or recrystallization.

The preferred embodiments of the present invention will now be further described with reference to specific examples. Variations and modifications of these embodiments can be effected without departing from the spirit and scope of the invention as described and claimed.

Unless otherwise stated, all percentages, parts and ratios therein are by weight.

A. PREPARATION OF INTERMEDIATES

EXAMPLE 1

(+)Ethyl 3-[(1-hydroxyprop-2(S)-yl)amino]acrylate
(V: $R_1$=ethyl)

3.76 g (50 mmol) of (+)-2-amino-1-propanol (IV) was added in 80 ml of acetonitrile and cooled to 0° C. To this, 5.07 ml (50 mmol) of ethyl propiolate (III, $R_1$=ethyl) was slowly added dropwise. The reactant mixture was stirred at a temperature not more than 5° C. for 8 hours and further stirred at room temperature for 1 hour.

Thereafter, the solvent was removed under reduced pressure (25° C./10 mmHg), to give 8.57 g of a colorless oily product (yield 99%).

Analysis of the product revealed that Z and E isomers were present in a ratio of 7:3 therein.

IR (KBr) cm$^{-1}$: 3330, 1660, 1600.

$[\alpha]^{20}_{589}$: +56.6° C. (CHCl$_3$, C=0.242)

NMR(CDCl$_3$) ppm: 7.65–7.82(1H×7/10, m), 7.50(1H×3/10, dd, J=13.3, 9.3H), 6.74(1H×7/10, dd, J=13.1, 8.1H), 4.82–4.88(1H×3/10, m), 4.78(1H×3/10, d, J=13.3H), 4.50 (1H×7/10, d, J=8.1H), 4.10–4.12(2H, q, J=7H), 3.41–3.72 (2H, m), 3.26–3.40(1H, m), 2.36(1H, brs), 1.25–1.26(3H, t, J=7H), 12.0(3H, d, J=6.8H)

EXAMPLE 2

(+)Ethyl 3-[(1-acetoxyprop-2(S)-yl)amino]acrylate
(VII: R=methyl, $R_1$=ethyl)

3.46 g (20 mmol) of (+)ethyl 3-[(1-hydoxyprop-2(S)-yl)amino]acrylate, 3.21 ml (23 mmol) of triethylamine and 0.244 g (2 mmol) of 4-dimethylaminopyridine were added in 50 ml of methylenechloride and cooled to 0° C. To this solution, 1.51 ml (22 mmol) of acetylchloride (VI, R=methyl) was slowly added dropwise. The reactant mixture was stirred for 30 minutes and then, the precipitate was filtered off.

Thereafter, the filterate was washed with 5 ml of aqueous 0.2N hydrochloric acid solution, 5 ml of aqueous sodium bicarbonate solution, and 5 ml of saturated saline water, in due order and then dried over magnesium sulfate. The organic solvent was completely removed under reduced pressure (25° C./20 mmHg), to give 4.22 g of an oily product (yield 98%).

Analysis of the product revealed that Z and E isomers were present in a ratio of 4:1 therein.

IR (NaCl) cm$^{-1}$: 3332, 1740, 1670, 1610.

$[\alpha]^{20}_{589}$: +65.31° C. (CHCl$_3$, C=0.222)

NMR(CDCl$_3$) ppm: 7.69–7.87(1H×3/4, m), 7.44(1H×1/4, dd, J=13.9H), 6.67(1H×3/4, dd, J=13.8H), 4.85–4.95(1H× 1/4, m), 4.79(1H×1/4, d, J=13H), 4.50(1H×3/4, d, J=8H), 4.11(2H, q, J=7H), 3.95–4.06(2H, m), 3.42–3.53(1H, m), 2.08(3H, s), 1.26(3H, t, J=7H)

B. PREPARATION OF THE PRODUCT

EXAMPLE 3

(+)Ethyl 2-(2,3,4,5-tetrafluoro)benzoyl-3-[(1-acetoxyprop-2(S)-yl)amino]acrylate (I: R=methyl, R$_1$=ethyl, X,X$_1$,X$_2$=fluoro)

1.08 g (5 mmol) of (+)ethyl 3-[(1-acetoxyprop-2(S)-yl) amino]acrylate and 0.77 ml (5.5 mmol) of triethylamine were added in 40 ml of acetonitrile and cooled to 0° C. To this solution, 1.12 g (5.25 mmol) of 2,3,4,5-tetrafluorobenzoyl chloride (VIII, X, X$_1$, X$_2$=fluoro) was slowly added dropwise. The reactant mixture was stirred for 30 minutes and then, the precipitate was filtered off.

Thereafter, the solvent was removed under reduced pressure (25° C./20 mmHg), to leave the residue which was subsequently added in 50 ml of methylene chloride and washed with 5 ml of aqueous saturated ammonium chloride solution, 5 ml of aqueous saturated sodium bicarbonate solution and 5 ml of saline water, in due order.

The solvent was dried over magnesium sulfate and removed completely under reduced pressure (25° C./20 mmHg), to give 1.90 g of an oily product (yield 97%).

Analysis of the product revealed that cis and trans isomers were present in a ratio of 3:1 or 1:3 herein.

IR (NaCl) cm$^{-1}$: 3230, 1740, 1700, 1620, 1560.

$[\alpha]^{20}_{589}$: +61.4° C. (CHCl$_3$, C=0.412)

NMR(CDCl$_3$) ppm: 9.39–10.95(1H, brs), 8.13 and 8.16 (1H, d), 7.08–7.16(1H×1/4, m), 6.96–7.04(1H×3/4, m), 4.04–4.24(2H, m), 4.04–4.08(2H, t, J=7H), 3.74–3.88(1H, m), 2.13(3H, s), 1.39 and 1.42(3H, d), 1.11(3H×3/4, t, J=7H), 0.98(3H×1/4, t, J=7H)

EXAMPLE 4

(+)Ethyl 2-(2-nitro-3,4,5-trifluoro)benzoyl-3-{(1-acetoxyprop-2(S)-yl)amino]acrylate (I: R=methyl, R$_1$=ethyl, X, X$_2$=fluoro, X$_1$=nitro)

1.08 g (5 mmol) of (+)ethyl 3-[(1-acetoxyprop-2(S)-yl) amino]acrylate and 0.78 ml (5.5 mmol) of triethylamine were added in 40 ml of acetonitrile and cooled to 0° C. To this solution, 2-nitro-3,4,5-trifluorobenzoyl chloride (VIII: X, X$_1$=fluoro, X$_2$=nitro) was slowly added dropwise. This reactant mixture was stirred for 30 minutes and then, a filtration procedure was carried out in the same manner with that of Example 3, to give 2.04 g of an oily product (yield 98%).

Analysis of the product revealed that cis and trans isomers were present in a ratio of 7:2 or 2:7 therein.

IR (KBr) cm$^{-1}$: 1740, 1700, 1640, 1550.

$[\alpha]^{20}_{589}$: +72.14° C. (CHCl$_3$, C=0.384)

NMR(CDCl$_3$) ppm: 9.54–10.91(1H, brs), 8.26(1H×2/9, d, J=14.8H), 8.17(1H×7/9, d, J=14H), 6.91–7.02(1H, m), 4.03 (2H, q, J=7H), 3.94–4.25(2H, m), 3.78–3.86(1H, m), 2.13 (3H; s), 1.40–1.43(3H, m), 1.12(3H×7/9, t, J=7H), 0.93(3H× 2/9, t, J=7H)

What is claimed is:

1. An optically active compound of (+)2-benzoyl-3-[(prop-2(S)-yl)amino]acrylate derivative having the formula I or the salts thereof:

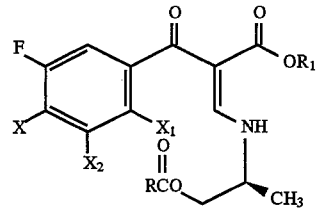

wherein X is a halogen; X$_1$ and X$_2$ are independently selected from a halogen and a nitro; and R and R$_1$ each is an alkyl group containing 1 to 4 carbon atoms.

2. The (+)2-benzoyl-3-[(prop-2(S)-yl)amino]acrylate derivative of claim 1, wherein said derivative is substantially optically pure.

3. The (+)2-benzoyl-3-[(prop-2(S)-yl)amino]acrylate derivative of claim 1, wherein R is methyl, R$_1$ is ethyl, and X, X$_1$, and X$_2$ are fluoro.

4. The (+)2-benzoyl-3-[(prop-2(S)-yl)amino]acrylate derivative of claim 1, wherein X and X$_2$ are fluoro and X$_1$ is nitro.

* * * * *